(12) United States Patent
Shehadi et al.

(10) Patent No.: US 11,667,877 B2
(45) Date of Patent: Jun. 6, 2023

(54) TISSUE PROCESSING APPARATUS, A FILTER AND A METHOD FOR PROCESSING TISSUE THEREFROM

(71) Applicants: Imad E. Shehadi, Madison, WI (US); Hisham Ramadan, Beirut (LB)

(72) Inventors: Imad E. Shehadi, Madison, WI (US); Hisham Ramadan, Beirut (LB)

( * ) Notice: Subject to any disclaimer, the term of this patent is extended or adjusted under 35 U.S.C. 154(b) by 560 days.

(21) Appl. No.: 16/640,037

(22) PCT Filed: Aug. 23, 2017

(86) PCT No.: PCT/IB2017/055078
§ 371 (c)(1),
(2) Date: Feb. 18, 2020

(87) PCT Pub. No.: WO2019/038577
PCT Pub. Date: Feb. 28, 2019

(65) Prior Publication Data
US 2020/0248127 A1 Aug. 6, 2020

(51) Int. Cl.
*C12M 3/00* (2006.01)
*A61M 1/00* (2006.01)
*B01D 24/00* (2006.01)
*C12M 1/26* (2006.01)
*C12M 1/00* (2006.01)
(Continued)

(52) U.S. Cl.
CPC ............ *C12M 33/14* (2013.01); *A61M 1/892* (2021.05); *C12M 21/08* (2013.01); *C12M 23/22* (2013.01);
(Continued)

(58) Field of Classification Search
CPC ...... C12M 33/14; C12M 21/08; C12M 23/22; C12M 29/00; C12M 41/44; C12M 47/12;
(Continued)

(56) References Cited

U.S. PATENT DOCUMENTS 5,624,418 A * 4/1997 Shepard ................. A61M 1/79
210/85
8,100,874 B1 1/2012 Jordan et al.
(Continued)

FOREIGN PATENT DOCUMENTS

WO 2014/174203 A1 10/2014
WO 2017/112455 A2 6/2017

OTHER PUBLICATIONS

International Search Report and Written Opinion for related International Application No. PCT/IB2017/055078, dated May 4, 2018; 12 pages.

*Primary Examiner* — Susan S Su
*Assistant Examiner* — Eric Rassavong
(74) *Attorney, Agent, or Firm* — Procopio, Cory, Hargreaves & Savitch LLP

(57) ABSTRACT

A tissue processing apparatus, a filter and a method for processing tissue therefrom #! The problem to be solved is to provide a portable apparatus for processing harvested fat to form a good quality graft that does not clog syringes, and the problem is solved by providing an apparatus as in the present invention with a filter that is inclined to the base of the apparatus and comprises of plurality of elongated protrusion that are structured at an angle on the surface of the filter and blocks the fibres when the harvested fat moves on the inclined surface of the filter, thereby filtering the harvested fat and avoiding clogging of syringes.

17 Claims, 9 Drawing Sheets

(51) Int. Cl.
*C12M 1/34* (2006.01)
*G01N 1/40* (2006.01)

(52) U.S. Cl.
CPC ............ *C12M 29/00* (2013.01); *C12M 41/44* (2013.01); *C12M 47/12* (2013.01); *A61M 1/88* (2021.05); *A61M 2202/0014* (2013.01); *A61M 2202/08* (2013.01); *A61M 2202/09* (2013.01); *B01D 23/00* (2013.01); *G01N 2001/4088* (2013.01)

(58) Field of Classification Search
CPC ...... C12M 45/02; C12M 47/02; C12M 47/04; A61M 1/892; A61M 1/88; A61M 2202/0014; A61M 2202/08; A61M 2202/09; B01D 23/00; G01N 2001/4088
See application file for complete search history.

(56) References Cited

U.S. PATENT DOCUMENTS

| | | | | |
|---|---|---|---|---|
| 8,815,099 B1* | 8/2014 | Dubois | ............... | A61M 1/79 |
| | | | | 210/488 |
| 8,858,518 B2* | 10/2014 | Schafer | ............... | A61M 1/0023 |
| | | | | 604/319 |
| 9,278,165 B2* | 3/2016 | Park | ............... | A61M 1/79 |
| 9,322,748 B1* | 4/2016 | Kimsey, II | ............... | A61M 1/0001 |
| 9,358,327 B1* | 6/2016 | Venturi | ............... | A61M 1/81 |
| 2008/0243028 A1* | 10/2008 | Howard | ............... | A61M 1/79 |
| | | | | 600/565 |
| 2010/0261242 A1 | 10/2010 | Harvey et al. | | |
| 2015/0352256 A1 | 12/2015 | Cimino et al. | | |
| 2015/0374888 A1* | 12/2015 | Shippert | ............... | A61M 1/0023 |
| | | | | 604/542 |

\* cited by examiner

TISSUE PROCESSING APPARATUS, A FILTER AND A METHOD FOR PROCESSING TISSUE THEREFROM

FIELD OF THE INVENTION

Present invention relates to a tissue processing apparatus, a filter and a method for processing tissue thereof, and more particularly relates to the tissue processing apparatus, the filter and the method for processing tissue for filtering harvested fat for preparing grafts that are used in fat augmentation, grafting or the like for different body parts.

BACKGROUND

The technology of fat grafting or fat augmentation has been widely used for restoration or recreation of shapes of different body parts like breasts, lips, cheeks etc. In such technologies, fat tissues from different donor site are transferred to the recipient site after performing purification of fat tissues. When the fat tissues are harvested from the donor site, various other substances like blood, oil, fiber etc. also comes along with the harvested fat and therefore, to prepare a good quality fat graft such additional substances have to be filtered without affecting the quality of the fat tissue for grafting. There are many devices available for preparing graft by using techniques like centrifugation etc. and involves various levels for separating additional substances such as blood, oil or the like using external suction means which requires external power supply. Thus, making the devices costly and heavier in size and therefore, it becomes very difficult to transport. Further, in many cases, the additional substances such as blood, oil etc. are easily filtered using the mesh filters of the devices because of its low viscosity, however, the substances such as fibres that are comparatively thick remains with the harvested fat even after filtration. The filtered fat tissues are grafted using syringes through cannulas into the recipient site of the body. In cases where the filtered fat tissue comprises of fibers, the fibers clog the syringes when the syringes are used for grafting the filtered fat tissues, thus increasing time for fat grafting. The presence of fibres in the filtered fat tissue may also affect the quality of the graft thereby affecting the quality of the surgery and the end result to the patients.

US publication number US2015352256 discloses a portable tissue collection and processing apparatus that comprises of a tissue retention volume and a filtrate volume separated by a mesh filter bag. The mesh filter bag filters the fluids from the washed biological material, which is sucked by external vacuum system and the tissues are retained in the tissue retention volume of the apparatus. The apparatus of this document provides a mesh filter bag for separating fluids from the tissue in the tissue retention volume and thereafter uses a rotatable shaft that disperses the additive from the washed biological material for processing adipose tissues, however, it is very likely that the processed adipose tissue of this apparatus may include fibers that while using for different augmentation process may result in clogging syringes. Furthermore, the apparatus of this document requires external vacuum system for sucking the fluids filtered by the mesh filter bag, and external power for rotating the shaft for dispersing the additive forms by means of handle, thereby making the apparatus complex and costly.

Therefore, the problem to be solved is to provide a portable apparatus for processing harvested fat to form a good quality graft that does not clog syringes, and the problem is solved by providing an apparatus as in the present invention with a filter that is inclined to the base of the apparatus and comprises of plurality of elongated protrusion that are structured at an angle on the surface of the filter and blocks the fibres when the harvested fat moves on the inclined surface of the filter, thereby filtering the harvested fat and avoiding clogging of syringes.

SUMMARY

According to an embodiment of the invention, a tissue processing apparatus comprising a container forming a closed volume with a bottom surface, a first opening on said container to receive a harvested fat, a filter including a plurality of elongated protrusion on a surface of said filter, and a second opening on said container to access said harvested fat filtered by said filter, wherein said surface of said filter forms an inclination with said bottom surface of said container and said plurality of elongated protrusion are structured at an angle on said surface of said filter for filtering said harvested fat received from said first opening such that when said harvested fat, moves on said surface of said filter, said elongated protrusion prevents fibers in said harvested fat to pass through said filter, thereby filtering said harvested fat.

According to an embodiment of the invention, the plurality of elongated protrusion is perpendicular to said surface of said filter.

According to an embodiment of the invention, the plurality of said elongated protrusion includes a passageway for allowing flow of said harvested fat through said elongated protrusions and blocking fibers.

According to an embodiment of the invention, the surface includes plurality of openings for filtering fluids from said harvested fat in said filter.

According to an embodiment of the invention, the plurality of openings that are structure to form a passage through said filter, said passage drains fluid from said harvested fat to said bottom surface by facing said bottom surface at an acute angle.

According to an embodiment of the invention, the container includes a third opening to remove fluids from said bottom surface of said container.

According to an embodiment of the invention, the filter is circumferentially connected to an inner surface of said container dividing said closed volume into two parts.

According to an embodiment of the invention, the container includes a base with at least two legs for supporting said container.

The According to an embodiment of the invention, the container includes a first transparent screen to monitor volume of said harvested fat filtered in said container.

According to an embodiment of the invention, the container includes a second transparent screen to monitor volume of fluid in said container.

According to an embodiment of the invention, a filter for a tissue processing apparatus comprising a surface for receiving a harvested fat and a plurality of elongated protrusion on said surface of said filter, wherein said surface of said filter when positioned inside said tissue processing apparatus forms an inclination with horizontal axis of said tissue processing apparatus, and said plurality of elongated protrusion are structured at an angle on said surface of said filter for filtering said harvested fat such that when said harvested fat moves on said surface of said filter, said elongated protrusion prevents fibers in said harvested fat to pass through said filter, thereby filtering said harvested fat.

According to an embodiment of the invention, the plurality of elongated protrusion is perpendicular to said surface of said filter.

According to an embodiment of the invention, the plurality of said elongated protrusion includes a passageway for allowing flow of said harvested fat through said elongated protrusions and blocking fibers.

According to an embodiment of the invention, the surface includes plurality of openings for filtering fluids from said harvested fat in said filter.

According to an embodiment of the invention, the plurality of openings are structure to form a passage at an acute angle with a bottom surface at horizontal axis of said tissue processing apparatus for draining fluids from said harvested fat.

According to an embodiment of the invention, a method for processing tissue in a tissue processing apparatus including the steps of receiving a harvested fat from a first opening on a container forming a closed volume with a bottom surface, filtering said harvested fat by a filter including a plurality of elongated protrusion structured at an angle on a surface of said filter forming an inclination with said bottom surface such that when said harvested fat received from said first opening, said harvested fat moves on said surface and, said elongated protrusion prevents fibers in said harvested fat to passing through said filter; and accessing said harvested fat after filtration from a second opening on said container According to an embodiment of the invention, the method includes filtering of said harvested fat by said elongated protrusions perpendicular to said surface of said filter.

According to an embodiment of the invention, the method includes filtering of said harvested fat by said elongated protrusion including a passageway for allowing flow of said harvested fat through said elongated protrusion and blocking fibers.

According to an embodiment of the invention, the method includes accessing said harvested fat from said second opening after monitoring volume of said harvested fat filtered by said filter on a first transparent screen on said container.

According to an embodiment of the invention, the method includes the filtering of said harvested fat by said filter including plurality of openings that structured to form a passage for draining fluids from said harvested fat to said bottom surface by facing said bottom surface at an acute angle.

According to an embodiment of the invention, the method includes the filtering of said harvested fat by said filter including removing fluids from said harvested fat on said bottom surface by a third opening on said container.

The According to an embodiment of the invention, the method includes removing of drained fluids from said third opening after monitoring volume of fluids on a second transparent screen on said container.

Figure 1:
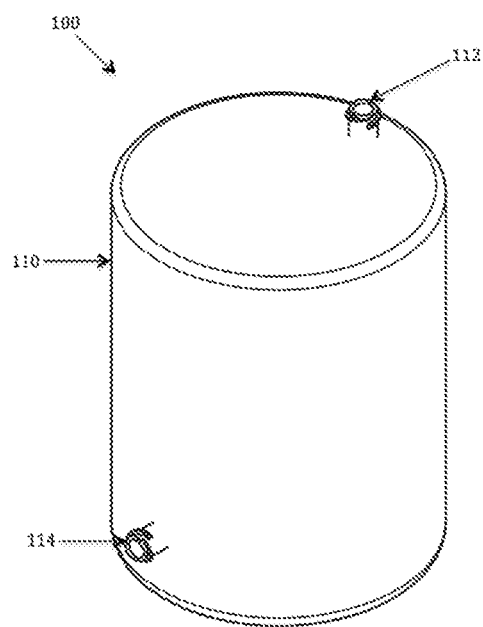
FIG. 1 represents an embodiment of the present invention depicting an isometric view of the container externally.

| Description of Elements | Reference Numeral |
| --- | --- |
| Tissue Processing Apparatus | 100 |
| Container | 110 |
| First opening | 112 |
| Second opening | 114 |
| Third opening | 116 |
| Bottom surface | 118 |
| Base | 120 |
| Legs | 122 |
| First transparent screen | 124 |
| Second transparent screen | 126 |
| Filter | 130 |
| Surface | 132 |
| Openings | 134 |
| Passage | 136 |
| Elongated protrusion | 138 |
| Passageway | 140 |

DETAILED DISCLOSURE OF THE INVENTION

The embodiments of the present invention can be understood by reading following detailed description of some of the embodiments with reference to the accompanying drawings.

In an embodiment of the present invention, a tissue processing apparatus (100) forms a sealed airtight system with three openings that are locked by the syringes. The tissue processing apparatus (100) comprises of a container (110) and a filter (130) for filtering harvested fat. The tissue is harvested from a donor site of a body and are processed for increasing the quality of graft. The container (110) for processing harvested fat forms a closed chamber or volume with a top surface, a bottom surface (118) and surrounding walls to enclose a volume.

As shown in FIG. 1, the container (110) of the apparatus (100) is a longitudinal cylindrical structure that comprises of a first opening (112) and a second opening (114). The first opening (112) on the container (110) receives harvested fat whereas the second opening (114) on the container (110) is for accessing filtered harvested fat. The first opening (112) on the container (110) is above the second opening (114) and the second opening (114) is on the vertical sides of the container for accessing the filtered harvested fat.

Figure 2A:
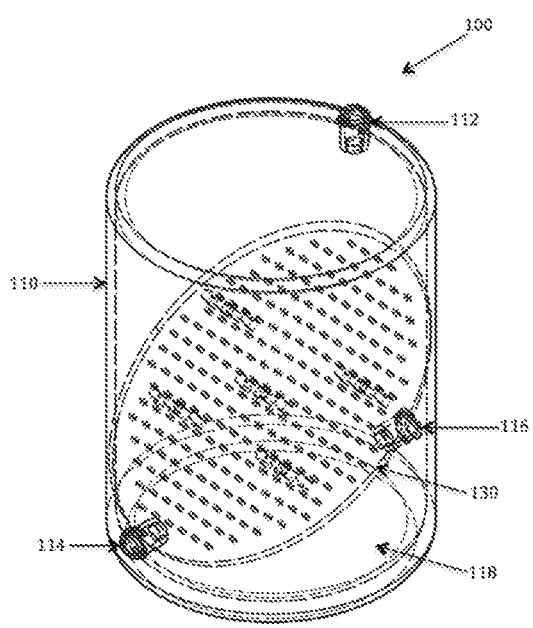
FIG. 2A represents an embodiment of the present invention depicting isometric view of the container with filter.
Figure 2B:
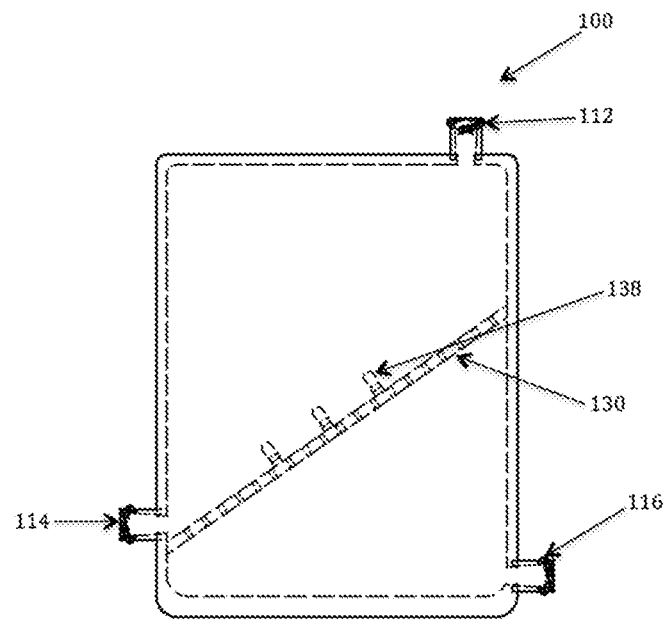
FIG. 2B represents an embodiment of the present invention depicting side view of the container with filter.
Figure 2C:
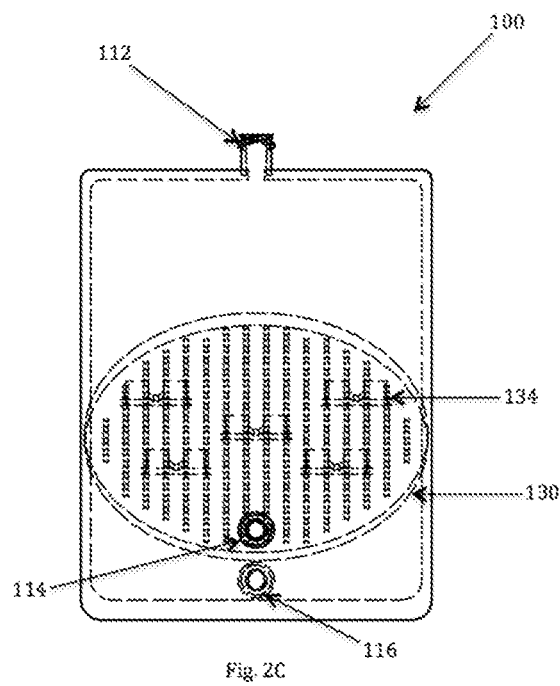
FIG. 2C represents an embodiment of the present invention depicting front view of the container with filter.

As shown in FIGS. 2A, 2B and 2C, the closed volume inside the container (110) is partitioned into two volumes by a filter (130) that is placed within the container (110). The filter (130) is placed or structured to form an inclination with respect to the bottom surface (118) of the container (110) or the horizontal axis of the container (110) i.e. forming a slope or elevation from one end to the other. The filter (130) forming the partition may be circumferentially connected to the inner surface of the vertical wall of the container (110). The filter (130) has a surface (132) that faces the top surface of the container (110) and since the filter (130) is inclined to the bottom surface (118) or top surface, the surface (132) of the filter (130) forming the slope uses the gravitational force for the movement of the harvested fat on it. The surface (132) of the filter (130) has a top end and a bottom end such that the height at the top end gradually slopes towards the bottom end. The first opening (112) is towards the top end of the surface (132) of the filter (130) such that when the first opening (112) of the container (110) receives the harvested fat, it falls on or near the top end of the filter (110) and moves or flows towards the bottom end of the filter (130). The bottom end of the filter (130) receives filtered harvested fat, which is accessible from the second opening (114) of the container (110). The second opening (114) is structured on the container above the bottom end of the surface (132) of the filter (130) such that the filtered harvested fat can be easily accessed from the bottom end of the filter (130). The surface (132) of the filter (130) includes plurality of opening (134) and protrusion (138) on its surface (132) facing the top surface of the container for filtering the harvested fat. Once the harvested fat moves or flows on the surface (132) of the filter (130), the fluids such as blood, serum or oil gets separated from the harvested fat and drains from the surface (132) through the opening (134) on the surface (132). The fluid from the opening (134) gets collected in the second volume on the bottom surface (118) and removed from the container (110) through third opening (116). The third opening (116) is structured on or near the bottom surface (118) such that once the fluid in the bottom surface (118) exceeds a predefined volume, they can be easily removed. The first opening (112), second opening (114) and the third opening (116) may have a luer lock structure that enables these openings to receive syringes or needles with luer lock structure.

Figure 3A:
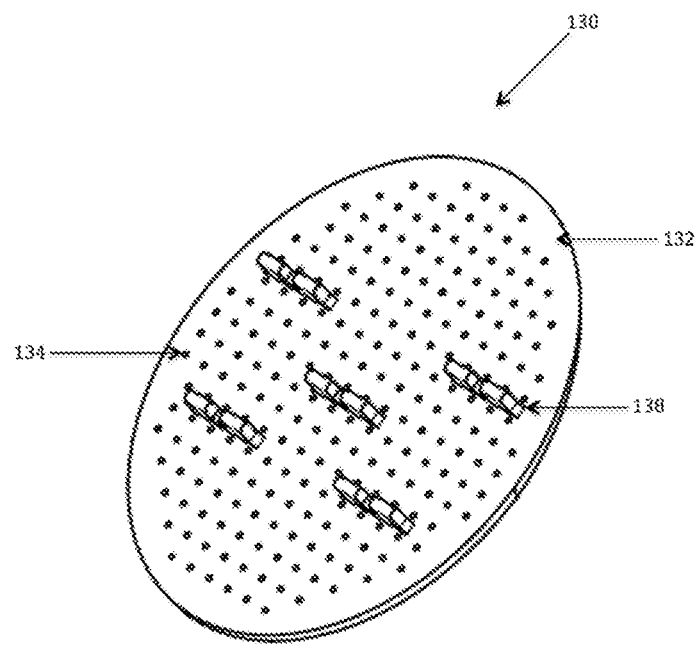
FIG. 3A represents an embodiment of the present invention depicting isometric view of the filter.
Figure 3B:
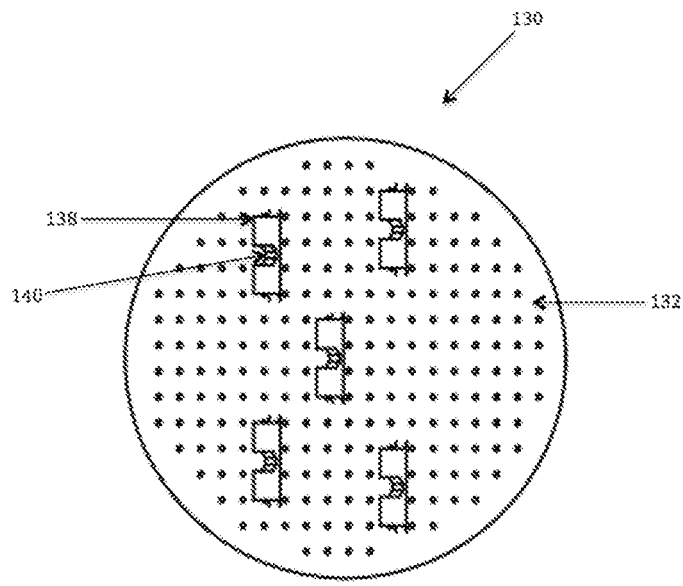
FIG. 3B represents an embodiment of the present invention depicting top view of the filter.
Figure 3C:
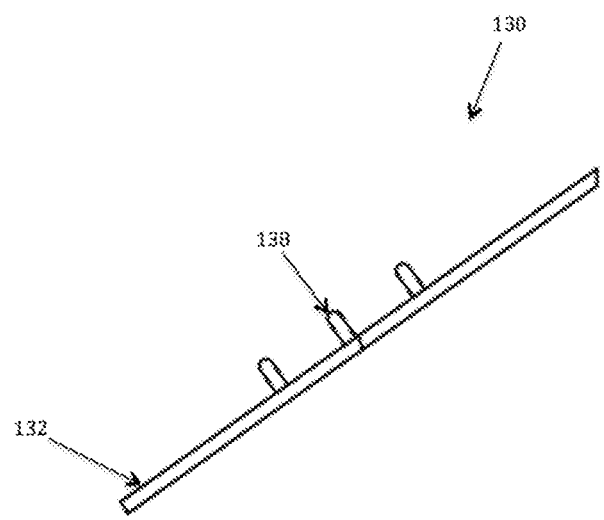
FIG. 3C represents an embodiment of the present invention depicting side view of the filter.
Figure 3D:
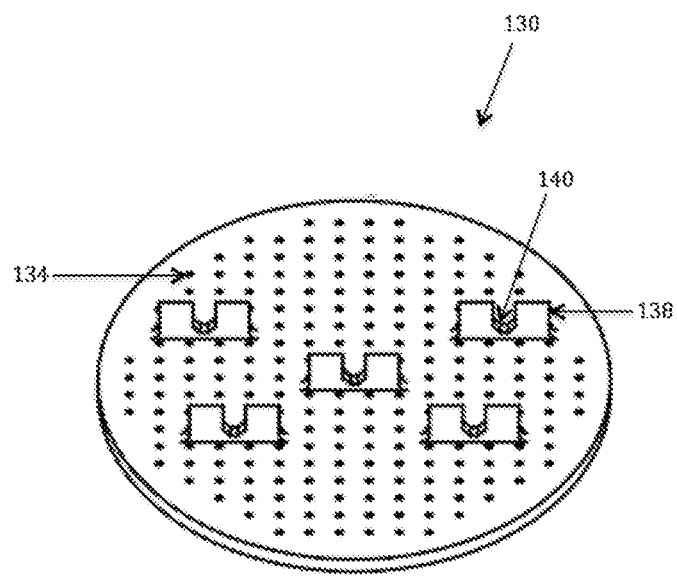
FIG. 3D represents an embodiment of the present invention depicting front view of the filter.
Figure 3E:
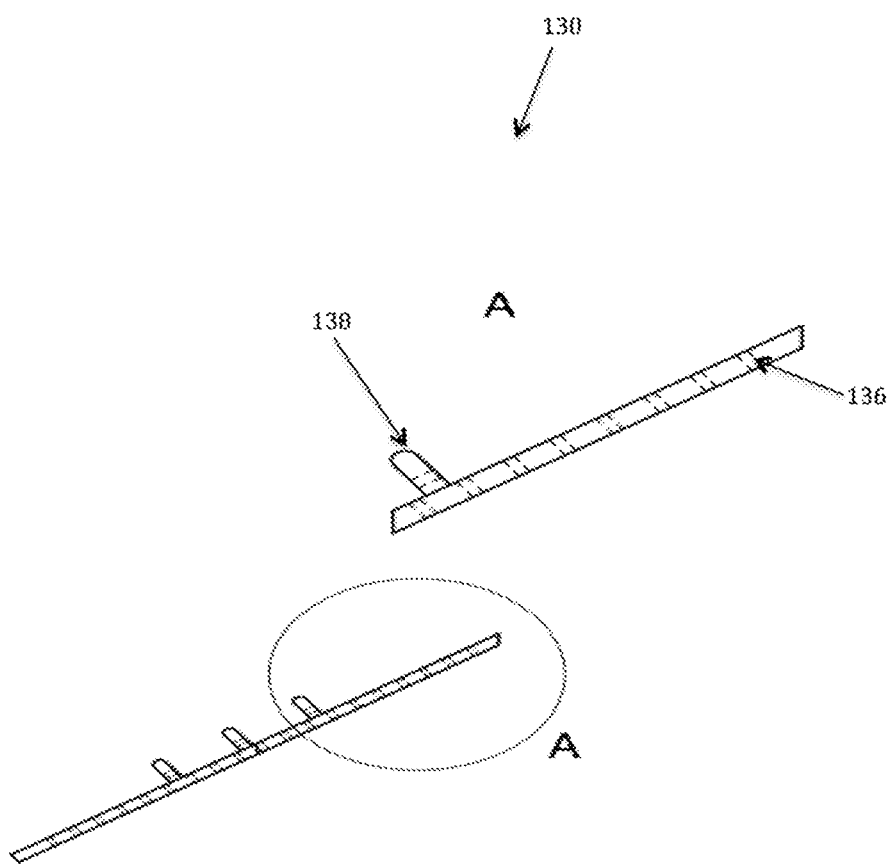
FIG. 3E represents an embodiment of the present invention depicting side enlarged view of the filter.
Figure 3F:
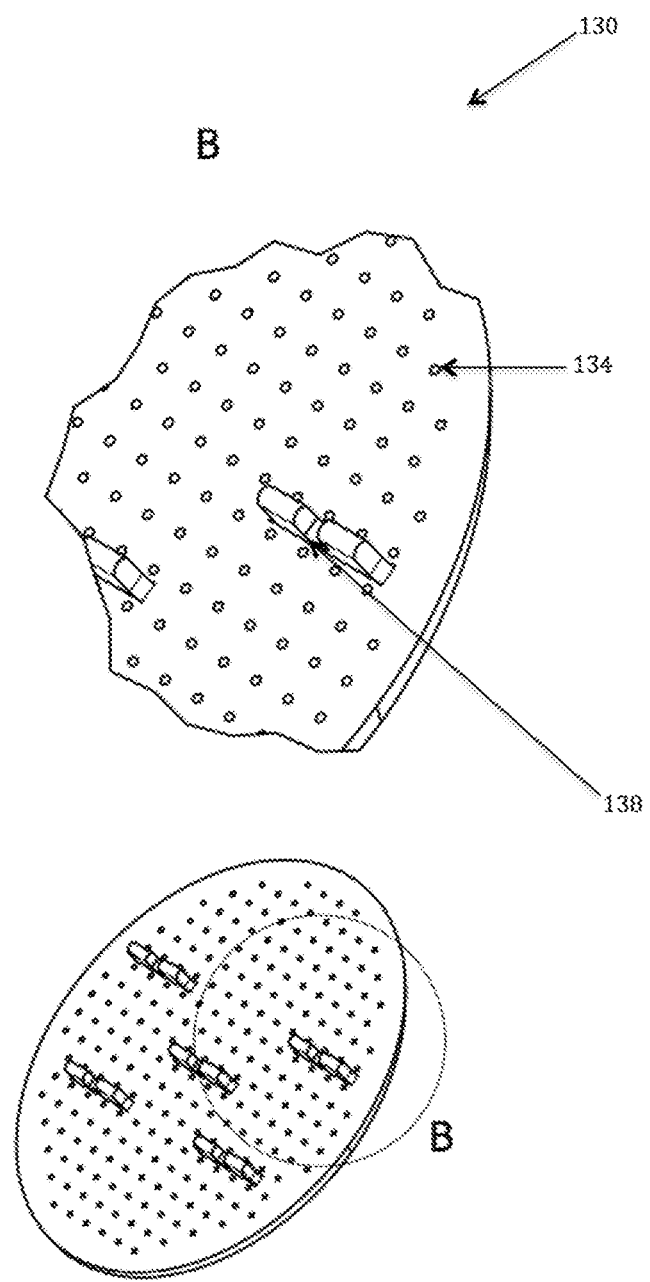
FIG. 3F represents an embodiment of the present invention depicting isometric enlarged view of the filter.

As shown in FIGS. 3A, 3B, 3C, 3D, 3E and 3F, the filter (130) can be a circular or disc shaped structure with a width and comprising of pluralities of elongated protrusion (138) and opening (134) on its surface (130) in a specific manner for filtering harvested fat. The elongated protrusion (138) can be a dam shaped structure on the surface (132) of the filter (130) for blocking the flow or movement of the fibrous tissue present in the harvested fat from the surface (132) of the filter (130). The plurality of elongated protrusion (138) is structured perpendicular to the surface (132) to create a barrier for blocking the smooth flow of fibrous tissue present in the harvested fat on the surface (132). The elongated protrusion (138) is placed in an alternate manner for example two are placed with a gap between them and the next may be ahead of the two elongated protrusions (138) and in front of the gap between the two elongated protrusions (138), thereby forming barricades for creating zigzag movement of the fibrous tissue present in the harvested fat on the surface (132) of the filter (130). This zigzag movement of the harvested fat on the surface (132) of the filter (130) block the fibers in the harvested fat. Further, the elongated protrusion (138) also includes a passageway (140) that forms a passage for allowing flow of harvested fat through the elongated protrusion (138). The passageway is open from the topside of the elongated protrusion (138) i.e. the opening of the passageway faces the top surface of the container and forms access through the elongated protrusion (138). The passageway (140) on the elongated protrusion (138) can be a U-shaped structure as shown in FIG. 3F(B) that allows passage of the harvested fat that is stucked between the fibers and blocked by the elongated protrusion (138). Thus, the combination of the plurality of the elongate protrusion (138) with passageway (140) on the surface (132) of the filter (130) allows passage of the harvested fat and blocks or prevents flow of fibers with it.

The plurality of opening (134) on the surface (132) of the filter (130) is structured to form a passage (136) as shown in FIG. 3E (A), for allowing fluids that comes along with the harvested fat like blood, serum etc. across the width of the filter (130). The passage (136) opens on the other side of the filter (130) to face the bottom surface (118) sideways rather than straight down i.e. the axis of the passage forms an acute angle with the bottom surface (118) or horizontal axis, thereby allowing substances like oil to drain from the surface (132) of the filter (130).

Figure 4A:
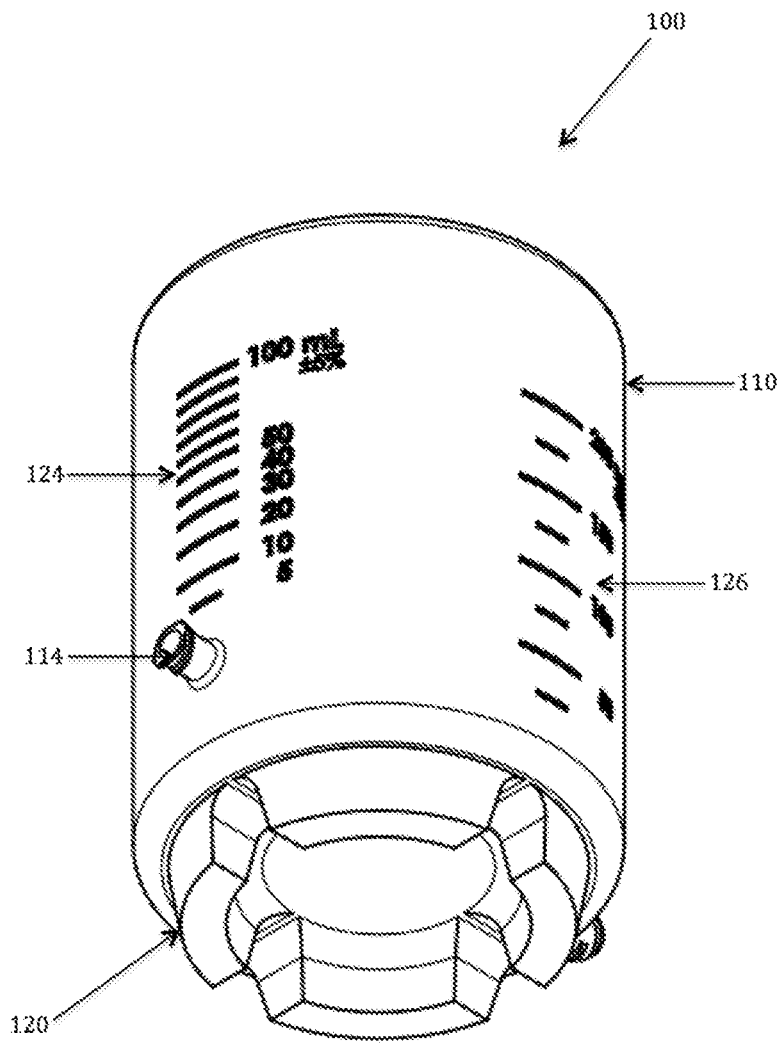
FIG. 4A represents an embodiment of the present invention depicting isometric view of the container with a base.
Figure 4B:
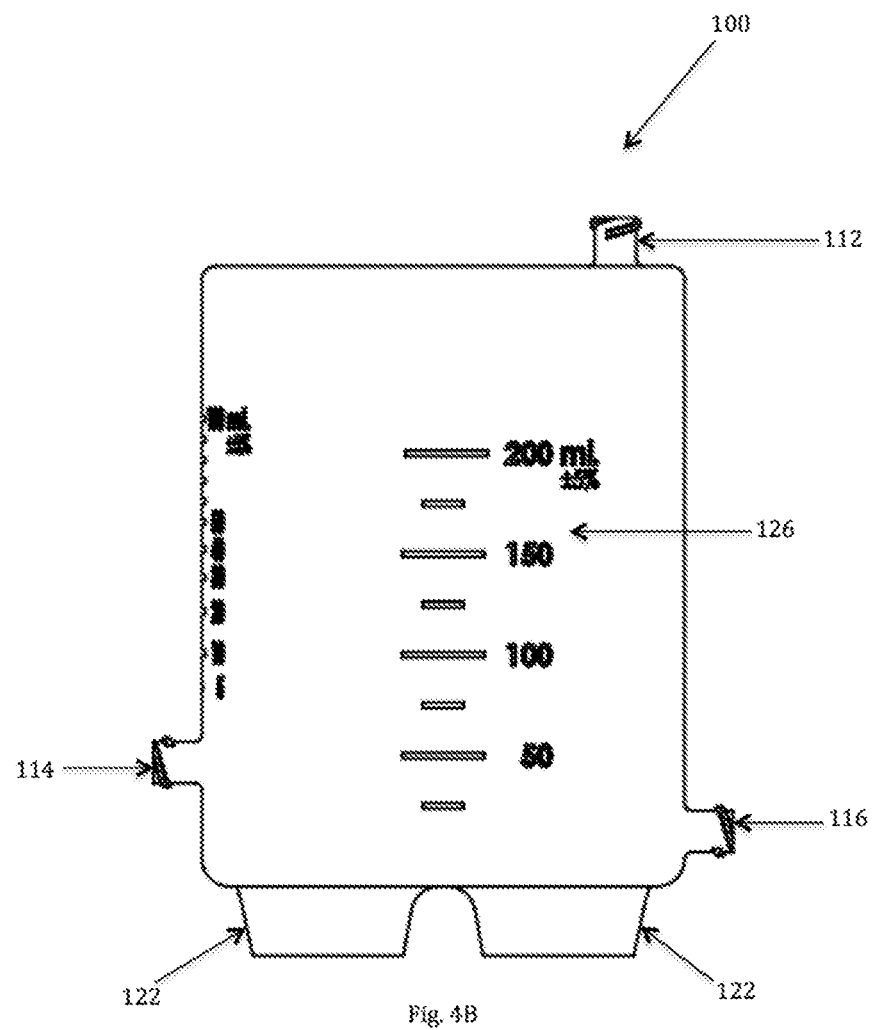
FIG. 4B represents an embodiment of the present invention depicting side view of the container with the base.
Figure 4C:
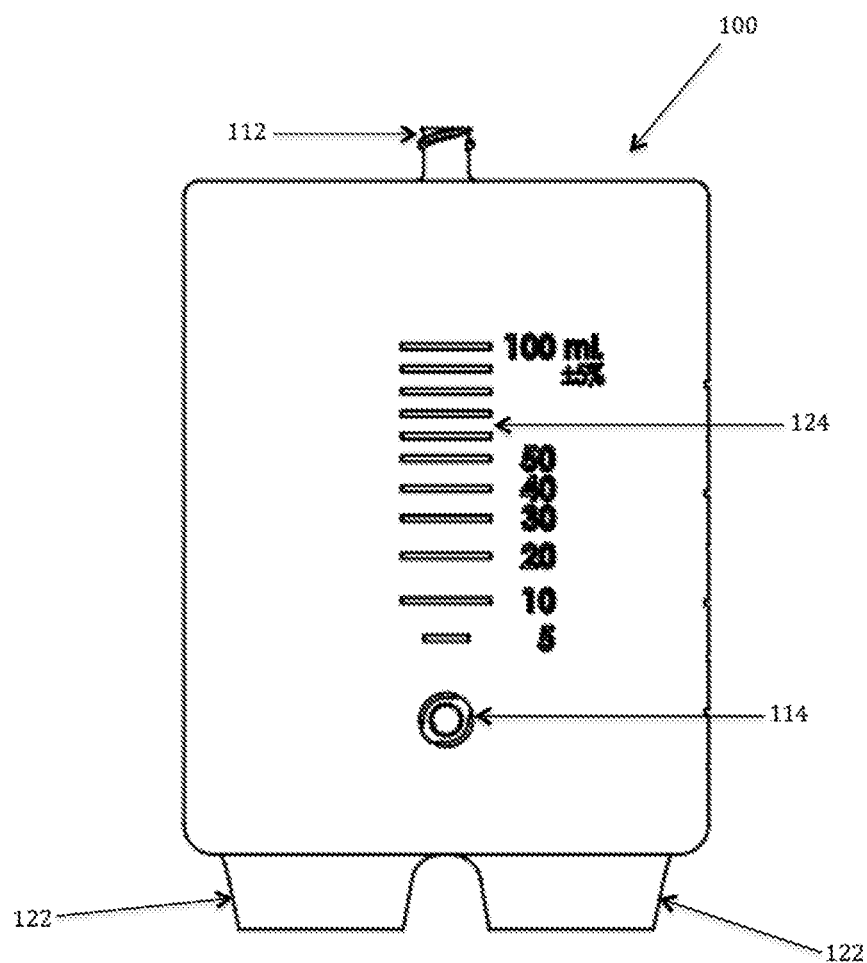
FIG. 4C represents an embodiment of the present invention depicting front view of the container with the base.

As shown in FIGS. 4A, 4B and 4C, the container (110) includes a base (120) that enables positioning of the container (110) on the table. The base (120) can have four legs (122) that are projected circumferentially with gaps in between the next legs and the opposite legs for enabling standing of the container. The container (110) also includes two transparent screens i.e. a first transparent screen (124) and a second transparent screen (126). The first transparent screen (124) is above the second opening (114) of the container (110) where the filtered fat gets collected. The first transparent screen (124) includes marks defining volume of the filtered fat ranging from 5 ml to 100 ml, as shown in FIG. 4C, and therefore, enables monitoring of the volume of the filtered fat available in the container (110). The second transparent screen (126) is on the vertical wall of the container (110) for monitoring the volume of the fluids separated from the harvested fat and stored on the bottom surface (118). The second transparent screen (126) also includes marks defining volume ranging from 50 ml to 200 ml. Once the volume of fluid reaches a predefined range or as per the user, the fluid can be removed from the container through the third opening (116) after monitoring from the second transparent screen (126).

Further, the tissue processing apparatus (100) can have various dimensions and scale while maintaining the same embodiment of the invention as disclosed above. Examples of variation in dimensions include reducing or increasing the bottom surface (118) of the container (110). Other modification can include elongating or shortening the height of the container (110). These modifications in dimensions will also produce size modification in the filter (130) and the filter surface (132). Such modification in filter surface (132) will result in modifying the quantity of the plurality of opening (134) on the surface (132) of the filter (130). This modification in quantity of opening (134) should maintain both the size of the opening (134) forming passage (136) as well as the spacing between the openings (134). Also, the size of the elongated protrusion (138) with the passageway (140) can remain the same or modified in a non-proportional way or substantially for the modification, which incurred on the container (100) or on the filter (130). On the other hand, the dimension and sizes of the first opening (112), second opening (114) and the third opening (116) may remain the same to allow proper connection to the syringe.

Also, the tissue processing apparatus (100) can be fabricated from various types of materials that can be sterilized. The material should withstand high autoclave temperature required to kill any Bacteria or any other microscopic pathogenic organism or the like, while at the same time not allowing the heat from the autoclave to deform or change the structure or the form of the Apparatus (100).

In an alternate embodiment, both the base (120) and legs (122) of the tissue processing apparatus (100) can be either an integrated part or a separate detachable part of the container (110). In the case the base (120) and legs (122) are detachable, the containers can be mounted on top of them by simple insertion. The base (120) and legs (122) can be manufactured from various materials.

The present invention is however not limited to the above embodiments disclosed above and referred in FIGS. 1 to 4 and other embodiments within the scope of the invention can be used for achieving the result of the present invention without limiting the scope of the invention.

The invention claimed is:

1. A tissue processing apparatus comprising:
   a container forming a closed volume with a bottom surface;
   a first opening on said container to receive a harvested fat including fibers;
   a filter including a surface with a top end to receive the harvested fat from the first opening, a bottom end, and a plurality of elongated protrusions structured at an angle on the surface of said filter for filtering fibers from the harvested fat; and
   a second opening on said container to access the filtered harvested fat from the bottom end of the surface of the filter,
   wherein the surface of the filter is inclined with respect to the bottom surface such that when the harvested fat is received at the top end from said first opening the harvested fat moves on the surface of said filter and the plurality of elongated protrusions prevents fibers of the harvested fat to pass through the surface of the filter, thereby filtering the harvested fat.

2. The tissue processing apparatus according to claim 1, wherein said plurality of elongated protrusions is perpendicular to said surface of said filter.

3. The tissue processing apparatus according to claim 2, wherein said plurality of elongated protrusions includes a passageway for allowing flow of said harvested fat through said plurality of elongated protrusions and blocking fibers.

4. The tissue processing apparatus according to claim 1, wherein the surface includes plurality of openings for filtering fluids from the harvested fat when the harvested fat moves on the surface of the filter.

5. The tissue processing apparatus according to claim 4, wherein said plurality of openings structured to form a passage through the surface of the filter, said passage drains fluid from said harvested fat to said bottom surface by facing said bottom surface at an acute angle.

6. The tissue processing apparatus according to claim 1, wherein said container includes a third opening to remove fluids from said bottom surface of said container.

7. The tissue processing apparatus according to claim 1, wherein said filter is circumferentially connected to an inner surface of said container dividing said closed volume into two parts.

8. The tissue processing apparatus according to claim 1, wherein said container includes a base with at least two legs for supporting said container.

9. The tissue processing apparatus according to claim 1, wherein said container includes a first transparent screen to monitor volume of said harvested fat filtered in said container.

10. The tissue processing apparatus according to claim 1, wherein said container includes a second transparent screen to monitor volume of fluid in said container.

11. A method for processing tissue in a tissue processing apparatus including the steps of:
    receiving a harvested fat including fibers from a first opening on a container forming a closed volume with a bottom surface;
    filtering fibers from the harvested fat by a filter including a surface with a top end, a bottom end, and a plurality of elongated protrusions structured at an angle on the surface of the filter that is inclined inclination with respect to the bottom surface such that when said harvested fat is received at the top end from said first opening, the harvested fat moves on said surface of the filter, and the plurality of elongated protrusions prevents fibers in said harvested fat to pass through the surface of the filter; and
    accessing the filtered harvested fat from the bottom end of the surface of the filter from a second opening on said container.

12. The method according to claim 11, including filtering of said harvested fat by said plurality of elongated protrusions perpendicular to said surface of said filter.

13. The method according to claim 12, including filtering of said harvested fat by said plurality of elongated protrusions including a passageway for allowing flow of said harvested fat through said plurality of elongated protrusions and blocking fibers.

14. The method according to claim 11, including accessing said harvested fat from said second opening after monitoring volume of said harvested fat filtered by said filter on a first transparent screen on said container.

15. The method according to claim 11, including filtering of said harvested fat by said filter including plurality of openings structured to form a passage for draining fluids from said harvested fat to said bottom surface by facing said bottom surface at an acute angle.

16. The method according to claim 14, including filtering of said harvested fat by said filter including removing fluids from said harvested fat on said bottom surface by a third opening on said container.

17. The method according to claim 15, including removing drained fluids from said third opening after monitoring volume of fluid on a second transparent screen on said container.

* * * * *